United States Patent [19]

Yamamoto et al.

[11] Patent Number: 4,487,760
[45] Date of Patent: Dec. 11, 1984

[54] HAIR COSMETICS

[75] Inventors: Hiromi Yamamoto, Chiba; Takeo Okumura, Sakura, both of Japan

[73] Assignee: Kao Soap Co., Ltd., Tokyo, Japan

[21] Appl. No.: 340,764

[22] Filed: Jan. 19, 1982

[30] Foreign Application Priority Data

Jan. 19, 1981 [JP] Japan .................................. 56-6219

[51] Int. Cl.$^3$ .......................... A61K 7/06; A61K 7/08
[52] U.S. Cl. ............................. 424/70; 424/DIG. 1; 424/47; 424/71
[58] Field of Search ......................... 424/70, 341, 342

[56] References Cited

U.S. PATENT DOCUMENTS 2,197,467  4/1940  Evans et al. ..................... 568/644 X
4,224,311  9/1980  Vanlerberghe et al. ............ 424/362

FOREIGN PATENT DOCUMENTS 3809M   1/1966  France .................................. 424/342
197607  7/1976  Japan ................................... 424/342
47809   9/1978  Japan ................................... 424/361

Primary Examiner—Dale R. Ore
Attorney, Agent, or Firm—Oblon, Fisher, Spivak, McClelland & Maier

[57] ABSTRACT

Hair cosmetics comprising as its effective component α-mono(methyl-branched alkyl) glyceryl ether of the formula

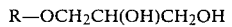

$$R-OCH_2CH(OH)CH_2OH$$

wherein R represents a methyl-branched saturated hydrocarbon group having 12-24 carbon atoms. The glyceryl ether is usually present in an amount of 0.5-30 wt % of the cosmetic composition.

2 Claims, No Drawings

HAIR COSMETICS

BACKGROUND OF THE INVENTION

1. Field of the Invention

This invention relates to hair cosmetics and more particularly, to hair cosmetics of good stability comprising a specific type of α-monoglyceryl ethers and capable of imparting to hair appropriate styling force and gloss, smoothness to the touch and good affinity for hair without involving any stimulativeness.

2. Description of the Prior Art

Generally employed oils for cosmetics include, for example, hydrocarbons such as liquid paraffin, squalene and the like, animal and plant oils, synthetic oils such as 2-octyldodecyl myristate, isopropyl myristate and the like, and lanolin.

However, these oils have the following drawbacks and are not satisfactory as hydrophilic oil. That is, hydrocarbons are a non-polar oil and when applied to hair, they show poor removability by washing because of the lack of affinity for water, so that they leave the residue on hair which exhibits disagreeable feeling to the touch. In addition, when these hydrocarbons are attached to clothes, there is the fear of causing a blot thereon. In recent years, liquid paraffin of low viscosity has been reported to have the possibility of causing the skin irritation. Animal and plant oils and synthetic oils are polar oils but show no hydrophilicity and cannot thus supplement moisture to hair, with the result that it is difficult to make hair smooth. When these oils are applied as hair tonic or hair liquid, their poor hydrophilicity is unfavorable and thus it is needed to use large amounts of solubilizing agents or dissolve them in an alcoholic solution of high concentration, either of which involves a problem from the viewpoint of scalp irritativeness or inflammability. Lanolin and its derivatives are hydrophilic in nature but have a problem in stable supply because it is of natural origin, coupled with another disadvantage that they are bad in color and offensive in odor and are paste-like or high in viscosity and are thus poor to the touch, showing limitations in application. Additionally, it has been reported that liquid paraffin has a fear of inducing allergy.

Accordingly, there is a demand of developing hydrophilic oils useful as a component of hair cosmetic.

The present inventors have intensively studied to develop hydrophilic compounds which show characteristic properties required for conventional oils, i.e. lubricating property, appropriate viscosity, excellent style retentivity, oily gloss and the like and, as a result, found that a specific type of α-monoalkyl glyceryl ethers meet the above requirement.

SUMMARY OF THE INVENTION

It is an object of the invention to provide a hair cosmetic comprising the just-mentioned type of α-monoalkyl glyceryl ethers which not only satisfies all the properties required for conventional hair cosmetics but also involves no skin irritativeness.

It is another object of the invention to provide a hair cosmetic which can supply moisture to hair and impart smoothness thereto.

It is a further object of the invention to provide a hair cosmetic which shows affinity for both hair and moisture.

According to the invention, there is provided a hair cosmetic which comprises 0.5–30 wt % of at least α-mono(methyl-branched alkyl) glyceryl ethers represented by the general formula (I)

$$ROCH_2CH(OH)CH_2OH \qquad (I)$$

in which R represents a methyl-branched saturated hydrocarbon group having 12–24 carbon atoms and the balance of known ingredients.

DETAILED DESCRIPTION AND EMBODIMENTS OF THE INVENTION

The α-mono(methyl-branched alkyl) glyceryl ethers used in the present invention are novel compounds and can be obtained by acting halogenating regents on an alcohol of the general formula (II)

$$ROH \qquad (II)$$

in which R has the same meaning as defined above to give a corresponding alkyl halide (III), reacting the alkyl halide with a glycerol alkali metal alcoholate in which hydroxyl groups at 2 and 3 positions have been protected to give a 1-alkyl glyceryl ether (IV) in which the hydroxyl groups at 2 and 3 positions have been protected, and then subjecting the ether (IV) to hydrolysis. The production process canC be expressed by the following series of reactions.

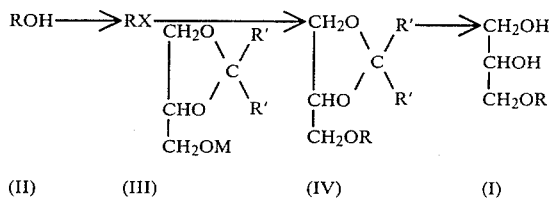

in which R' represents a lower alkyl group or phenyl group, M represents an alkali metal, and R has the same meaning as defined hereinbefore.

The production of the alkyl halide (III) from the alcohol (II) is feasible by the ordinary technique of converting alcoholic hydroxyl groups into halogens. For instance, known halogenating reagents including chlorinating reagents such as thionyl chloride, phosphorus trichloride, phosphorus pentachloride and the like, brominating reagents such as phosphorus tribromide, phosphorus pentachloride, mineral acid/hydrobromic acid and the like, and iodinating reagents such as red phosphorus/iodine are acted on the alcohol under ordinary conditions to obtain alkyl halides (III) in high yeild.

Then, the alkyl halide (III) and a glycerol alkali metal alcoholate whose hydroxyl groups at 2 and 3 positions have been suitably protected are caused to react with each other to give a 1-alkyl glyceryl ether (IV) whose hydroxyl groups at 2 and 3 positions have been protected. In order to protect the hydroxyl groups at 2 and 3 positions, ketones are conveniently used and most conveniently acetone is used. The alkali metals for the alcoholate are suitably sodium or potassium. The alkali metal or its hydroxide is reacted with an intended glycerol to obtain an alcoholate. The production of the ether (IV) from the alkyl halide (III) and the alcholate can be carried out under ordinary etherifying conditions. In general, the reaction is completed, without use of any catalyst, only by heating in suitable solvent. The alcoholate is used in an amount of about 1–5 moles, preferably about 2–3 moles, per mole of the alkyl halide (III) and the reaction is conducted at 120°–160° C., preferably 140°–160° C., for several hours. In the best mode of the embodiment, about 3 moles of sodium alcoholate of isopropylidene glycerol per mole of an alkyl chloride (III, X=Cl) is heated under reflux in xylene solvent for several hours.

Subsequently, the 1-alkyl glyceryl ether (IV) whose hydroxyl groups at 2 and 3 positions have been protected is hydrolyzed in the presence of a mineral acid catalyst to remove the protecting groups, thereby obtaining an intended alkyl glyceryl ether (I). The mineral acids may be any of sulfuric acid, hydrochloric acid, nitric acid and phosphoric acid, among which sulfuric acid is most beneficial. It is convenient to use 0.5–3.0 N, preferably 1.0–2.0 N, mineral acid in the practice of the invention. The hydrolysis is suitably effect at temperatures of 50°–100° C. and most conveniently, lower alcohols such as methanol, ethanol and the like are added and the reaction system is refluxed at their boiling point.

Alternatively, the α-mono(methyl-branched alkyl) glyceryl ether (I) of the present invention may be prepared by reacting an epihalohydrin with the alcohol (II) to give an alkylhalohydrin ether (V), ring-closing the ether to give an alkyl glycidyl ether (VI), and hydrolyzing the glycidyl ether. This process can be expressed by the following series of reactions:

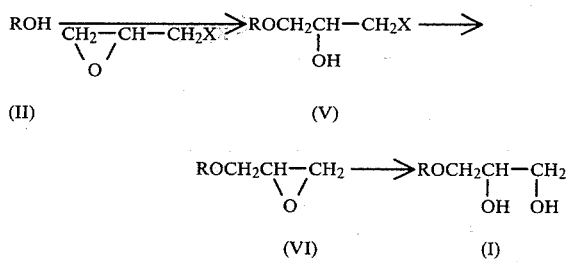

(in which X represents a halogen atom and R has the same meaning as defined hereinbefore).

The reaction between the alcohol (II) and the epihalohydrin is most preferably conducted in the presence of mineral acids, Lewis acids or bases in an amount of 1–5 moles of the alcohol per mole of the epihalohydrin at a temperature ranging from about 80° C.–120° C. The epihalohydrin includes epichlorohydrin or epibromohydrin.

The ring-closing glycidylating reaction of the alkyl halohydrin ether (V) can be effected under ordinary ring-closing reaction conditions of halohydrin. That is, an alkali catalyst is added to the halohydrin (V), followed by heating to obtain the glycidyl ether (VI). The halohydrin (V) which has been obtained in the preceding step can be served for the ring-closing reaction as it is without isolating it. In this case, it is preferable to heat the system at a temperature of about 50°–150° C. after addition of about 1–5 moles of an alkali per mole of the employed epihalohydrin. Preferable examples of the alkali include alkali metal hydroxides such as sodium hydroxide, potassium hydroxide and the like, and alkali metal carbonates such as sodium carbonate.

When the alkyl glycidyl ether (VI) is ring opened under ordinary epoxide ring-opening conditions, an intended α-mono(methyl-branched alkyl) glyceryl ether (I) can be obtained. The ring opening is usually conducted by hydrolysis with an acid catalyst, i.e. it is favorable to heat the reaction system together with an aqueous solution of a mineral acid such as sulfuric acid, hydrochloric acid, nitric acid or phosphoric acid. The mineral acid has suitably a concentration of about 0.1–5 N. The reaction is completed when the reaction system using an ether solvent such as diethylene glycol dimethyl ether is heated at a temperature of 80°–150° C. for several hours.

The alcohol (II) which is one of the starting materials for the α-monomethyl-branched alkyl glyceryl ether can be obtained by subjecting a corresponding carboxylic acid ester to the high pressure catalytic reduction using, for example, a copper-chromium catalyst. Examples of the corresponding carboxylic acid include acids which are obtained as a by-product at the time of the production of, for example, oleic acid dimer and is mainly composed of isostearic acid of the general formula (VII)

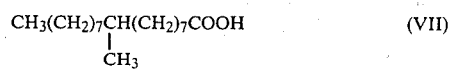

Among the thus obtained α-mono(methyl-branched alkyl)-glyceryl ethers, preferable ethers are those of the general formula (I) in which R is a group of the following formula (VIII)

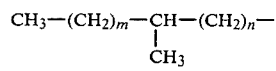

in which m is an integer of 2–14, n is an integer of 3–11 provided that m+n is an integer of 9–21, preferably 11–17. Above all, the ester in which the acid moiety of the formula (VIII) is composed of over 75% of a group having 18 carbon atoms and m in the formula (VIII) is an integer of 6–8 is preferable.

As will be appreciated from the above, it is preferable that the branched chain of the α-mono(methyl-branched alkyl) glyceryl ether is near the center of the main alkyl chain. In this regard, industrially produced alcohols (ii) are obtained as a mixture of alcohols having certain distributions in total of carbon atoms in the alkyl group and in position of the branched methyl group. For instance, isostearyl alcohol to be a reduction product of the isostearic acid having the methyl branching which has been obtained as by-product at the time of production of oleic acid dimer as mentioned above contains over about 75% of alcohols whose carbon atoms are 18 in number (the sum of m and n is 15), and the balance of alcohols having 14, 16 and 20 carbon atoms, the branched methyl group being positioned approximately at the center of the alkyl main chain (J. Amer. Oil Chem. Soc. 51, 522 (1974)). Accordingly, this alcohol can be conveniently used in the practice of the invention.

The α-mono(methyl-branched alkyl) glyceryl ethers are liquid at room temperature, and are free of any double bonds and ester bondings, so that they are chemically stable. In addition, they do not show any skin irritativeness. The physical properties of a typical α-mono(methyl-branched alkyl) glyceryl ether are shown below.

| Methyl-branched alkyl group | Melting Point | Specific Gravity (30° C.) | Viscosity (30° C.) |
|---|---|---|---|
| Mainly composed of group (VIII) where m = 7 and n = 8 | 23° C. | 0.912 | 856 |

The hair cosmetic composition according to the invention can be prepared in a usual manner by adding 0.5-30 wt %, preferably 1.0-15 wt %, (hereinafter referred to simply as %) of at least one mono(methyl-branched alkyl) glyceryl ether to other known cosmetic ingredients and then agitating the mixture.

The known cosmetic ingredients include, for example, known oil bases for cosmetic, emollients, gelating agents, various emulsifiers, perfumes, preservatives such as parahydroxybenzoate, antioxidants such as butylhydroxyanisole, colorants such as dyes, refrigerants such as menthol, bactericides such as hinokitiol, wetting agents such as propylene glycol, solvents such as alcohols, water and the like. These ingredients has no limits on application and are formulated appropriately as required.

The thus obtained hair cosmetics may be used in various forms including, for example, hair tonic, hair conditioner, pomade, cosmetic, hair oil, hair cream, hair liquid, hair spray, set lotion, hair treatment and the like.

These hair cosmetics are free of various drawbacks as will be involved in conventional oils and exhibit excellent properties in respect of skin irritativeness and feeling to the touch.

The present invention is more particularly described by way of references and examples, which should not be construed as limiting the invention thereto. Preparation of starting alcohol (formula (II)) is also shown in reference.

REFERENCE 1

Into a 20 l autoclave charged were 4770 g of isopropyl isostearate (Emery 2310 isopropyl isostearate commercially available from U.S. Emery Co., Ltd.) and 239 g of a copper-chromium catalyst (Nikki K.K.). Then, hydrogen gas was charged at a pressure of 150 kg/cm$^2$ and the reaction mixture was heated up to 275° C. After the hydrogenation under 150 kg/cm$^2$ at 275° C., the reaction product was cooled and the catalyst residue was removed by filtration to obtain 3500 g of a crude product. The crude product was distilled under reduced pressure to obtain 3300 g of colorless transparent isostearyl alcohol as a distillate of 80°-167° C./0.6 mmHg. The thus obtained isostearyl alcohol (methyl-branched stearyl alcohol) had an acid value of 0.05, a saponification value of 5.5, and a hydroxyl value of 181.4. This product showed absorption peaks at 3340, 1055 cm$^{-1}$ in the IR analysis (liquid film) and at $\delta$3.50(broad triplet, —CH$_2$—OH) in the NMR analysis (CCl$_4$ solvent). The main components of this alcohol were found by gas chromatograph to be composed of a mixture of about 75% of alcohols whose alkyl group had 18 carbon atoms in total (the sum of m and n being 10 in the formula (II)) and the balance of alcohols whose alkyl group had 14 and 16 carbons atoms, respectively, the branched methyl group being joined around the central portion of the alkyl main chain in all the cases.

REFERENCE 2

(i) 2444 g of the isostearyl alcohol obtained in Reference 1 was charged into a 5 l reaction vessel equipped with a thermometer, a reflux condenser, a dropping funnel, a nitrogen gas-introducing tube and an agitator. Thionyl chloride was dropped from the dropping funnel in the stream of nitrogen gas at room temperature while agitating. The reaction mixture generated heat and simaltaneously a gas was generated. The reaction mixture was raised to a temperature of 31° C. at an initial stage of the reaction but the temperature gradually decreased with an increase in amount of thionyl chloride and decrease down to about 18° C., whereupon the reaction mixture was heated to about 40° C., followed by further dropping thionyl chloride. After the generation of the gas became gentle, the reaction mixture was again heated to 70°-80° C. whereupon the gas generated violently and thionyl chloride was subsequently dropped. At the time when no generation of the gas was recognized, the dropping of thionyl chloride was stopped. The total amount of dropped thionyl chloride amounted to 2200 g. The reaction product was cooled and continuedly agitated at 70°-80° C. for further 1 hour.

The reaction product was cooled and distilled at 40°-50° C. to remove low boiling point distillates (mainly composed of unreacted thionyl chloride) therefrom and the resulting residue was ice-cooled and ice blocks were added thereto portion by portion while agitating. After it has been confirmed that violent generation of the gas was stopped, an ether and then water were added and the mixture was sufficiently agitated. The ether layer was collected and neutralized with sodium bicarbonate, followed by distilling off the solvent and distilling under reduced pressure to obtain 2217 g of isostearyl chloride from a distillate of 103°-163° C./0.1-1.0 mmHg.

IR (liquid film) : 725, 650 cm$^{-1}$

NMR (CCl$_4$) : $\delta$ 3.50 (triplet, -CH$_2$Cl)

(ii) Into a 5 l reaction vessel equipped with a thermometer, an agitator, dropping funnel and the Dienstark trap were charged 798 g of isopropylidene glycerol, 1500 ml of xylene, 340 g of a 93% sodium hydroxide solution and 300 g of water, followed by heating 130°-140° C. and refluxing while agitating. Water was separated in the Dienstark trap from the distilled water/xylene mixture to remove it outside the reaction system and the xylene was returned to the system. After heating under reflux for about 16 hours, distillation of water was not recognized, whereupon 777 g of the isostearyl chloride obtained in (i) was dropped from the dropping funnel in about 30 minutes. After completion of the dropping, the reaction mixture was further heated under refluxed for about 9 hours at 130°-140° C. to complete the reaction. After cooling, the sodium chloride precipitated in the reactor was removed by filtration and the solvent was distilled off under reduced pressure to obtain 800 g of a distillate of 176°-206° C./0.25-0.50 mmHg. This was confirmed to be 2,3-0-isopropylidene-0-isostearyl glyceryl ether.

IR (liquid film):cm$^{-1}$ 1200-1260, 1050-1120 (C-O stretching vibration)

NMR (CCl$_4$):$\delta$ 3.1-4.2 (multiplet,

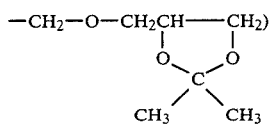

(iii) Into a 5 l reactor equipped with an agitator, a thermometer and a reflux condenser was charged 1103 g of isopropylideneisostearyl glyceryl ether obtained in (ii), to which were added 1500 ml of ethanol and 2000 ml of 0.1N sulfuric acid. The reaction mixture was heated under reflux at 80°–85° C. with agitation. About 10 hours after the heating, it was confirmed by the gas chromatograph that the isopropylideneisostearyl glyceryl ether was completely hydrolyzed. The reaction system was allowed to stand thereby separating it into an oil phase and an aqueous phase. The aqueous phase was extracted with ether and the resulting extract was combined with the oil phase, to which was added an aqueous sodium bicarbonate solution to neutralize the remaining acid therewith. After collecting the organic phase, the solvent was distilled off under reduced pressure, followed by thermally drying at 100° C./0.1 mmHg for 3 hours, thereby obtaining 900 g of α-mono(isostearyl) glyceryl ether in the form of a colorless transparent liquid.

IR (liquid film):3400, 1050–1140 cm$^{-1}$
NMR (CCl$_4$):δ
3.2–3.8 (multiplet,

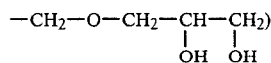

Acid value: 0.08, Saponification value: 0.36, Hydroxyl value: 313.8, Iodine value: 0.32

REFERENCE 3

(i) Into a 3 l reactor equipped with a thermometer, a reflux condenser, a dropping funnel and an agitator was charged 250 g (0.93 moles) of isostearyl alcohol obtained in Reference 1, to which was added 2 ml of boron trifluoride-diethyl ether complex at room temperature while agitating. The mixture was raised to a temperature of 85° C, into which was dropped 150 g (1.63 moles) of epichlorohydrin from the dropping funnel in about 2 hours. Since the reaction was exothermic, the mixture was so cooled that the temperature was within the range of 100°–110° C. to keep the reaction temperature. After completion of the dropping, the temperature was held at 100° C. for 3 hours and the agitation was continued. The gas-chromatographic analysis revealed that a ratio of unreacted alcohol to isostearyl chlorohydrin ether was 1:3.

(ii) 400 G of an aqueous 40% sodium hydroxide solution was dropped from the dropping funnel while agitating, into the reaction product of (i) without isolating the isostearyl chlorohydrin ether, followed by dropping 400 g of tertiary butyl alcohol. After completion of the dropping, the mixture was heated under reflux while agitating at 80° C. for 2 hours. Simultaneously with commencement of the agitation, salt began to precipitate and increased in amount with a lapse of time. The reaction was traced by gas chromatograph and when it was confirmed that the chlorohydrin ether completely disappeared, the reaction was stopped. The precipitated salt was removed by filtration and the resulting filtrate was allowed to stand and separated into an oil phase and an aqueous phase. The oil phase was distilled under reduced pressure to remove the solvent therefrom. Then, 50 g of unreacted alcohol was obtained and finally 170 g of isostearyl glycidyl ether to be a distillate of 160°–170° C./0.4 mmHg was obtained.

IR (liquid film):cm$^{-1}$
1250, 1100, 920, 845
NMR (CCl$_4$):δ
2.3–3.7 (multiplet,

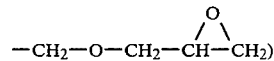

(iii) Into a 3 l reactor equipped with an agitator, a thermometer, a reflux condenser and a dropping funnel were charged 140 g of isostearyl glycidyl ether obtained in (ii) and 400 ml of diethylene glycol dimethyl ether. Then, 800 ml of 0.5N sulfuric acid was dropped into the mixture from the dropping funnel while agitating. After completion of the dropping, the mixture was heated to 100°–110° C., at which it was continuedly agitated for about 8 hours. The gas chromatograph revealed that the glycidyl ether completely disappeared. The reaction product was cooled and allowed to stand, so that it separated into an oil phase and an aqueous phase. The aqueous phase was extracted with ether and the resulting extract was combined with the oil phase, to which was added sodium bicarbonate to neutralize the remaining acid therewith. The oil phase was collected and distilled under reduced pressure to remove the solvent, followed by heating and drying at 100° C./0.1 mmHg for 3 hours. As a result, 120 g of a colorless transparent liquid was obtained. The gas-chromatography, IR and NMR chracteristics of this product were coincident with those of α-mono(isostearyl) glyceryl ether obtained in Example 1 appearing hereinafter.

EXAMPLE 1

Hair creams comprising α-mono(isostearyl) glyceryl ethers used in the present invention and shown later and several compounds for comparison were prepared to evaluate their skin irritativeness and feeling on use.

The skin irritativeness was evaluated as follows: Each hair cream was subjected to an open patch test for successive four days using three groups of rats, each group consisting of 6 rats, and an intensity of the skin reaction at the 5th day was evaluated. The evaluation was conducted according to the following standards:

No. reaction (−), Redness (+), Chemosis (++)

The feeling on use was evaluated by an organoleptic test made by ten panel members according to the following standards: (+2) Very good, (+1) Relatively good, (0) Moderate (−1) Relatively poor

| Composition of Hair Cream: | |
| --- | --- |
| Tested compound | 4(%) |
| Liquid paraffin | 10 |
| Bees wax | 3 |
| Cetanol | 2 |
| Polyoxyethylene sorbitan monostearate | 3 |
| Methylparaben | 0.1 |
| Butylparaben | 0.1 |
| Water | Balance |

TABLE 1

| Tested Compound | Skin Irritativeness | Other changes in Skin |
|---|---|---|
| Inventive Compound | | |
| α-mono(isostearyl)glyceryl ether (M = 7, n = 8 in group of (VIII)) | (±) | No changes |
| α-mono(isopalmityl)glyceryl ether (m = 7, n = 6 in group of (VIII)) | (±) | " |
| Comparative Compound | | |
| α-monooleyl glyceryl ether (selachyl alcohol) | (+) | Skin dregs were recognized. |
| Monoglyceride oleate | (++) | Very intense skin reaction. |
| Monoglyceride stearate | (+) | Slight gloss. |
| Sorbitan monooleate | (±) | " |
| Water | (−) | No changes |

TABLE 2

| | Tested Compound | Ease in hair set | Set Retentivity | Stickiness | Gloss | Spreading | Feeling | Hardness |
|---|---|---|---|---|---|---|---|---|
| Inventive Compound | α-mono(isostearyl)glyceryl ether | +1.8 | +1.2 | −0.9 | +1.6 | +0.3 | +1.8 | −0.2 |
| | α-mono(isopalmityl)glyceryl ether | +1.8 | +0.9 | −1.1 | +1.0 | +0.2 | +1.6 | 0.0 |
| Comparative Compound | α-monooleyl glyceryl ether (selachyl alcohol) | −1.1 | +1.2 | +1.1 | +0.1 | +0.2 | +0.2 | −1.4 |
| | Monoglyceride oleate | +1.4 | +1.1 | +1.8 | −0.1 | +0.1 | +0.1 | −0.2 |
| | Sorbitan monooleate | +0.1 | +0.2 | +0.1 | −1.3 | +0.2 | +1.4 | +0.2 |
| | Sorbitan sesquioleate | +0.2 | +0.9 | +0.9 | −0.9 | −0.1 | −1.1 | −0.1 |
| | Monoglyceride stearate | −1.8 | −1.4 | −1.1 | −1.8 | −1.2 | +0.2 | −1.1 |

(Note 1.)
The figures in the table show the respective average values of 10 panel members.
(Note 2.)
In the column of the "Stickiness", the negative value is better than the poritive one.

The results of these tests reveal that the hair creams comprising the α-mono (methyl-branched alkyl) glyceryl ethers according to the invention are lower in skin irritativeness, more excellent in ease in hair setting, lower in stickiness and better in gloss than the conventional creams.

EXAMPLE 2

Hair Cream (Composition)

| (1) α-mono(isostearyl)glyceryl ether | 12.5(%) |
|---|---|
| (2) Polyoxyethylene stearyl ether | 1.5 |
| (3) Bees wax | 1.0 |
| (4) Perfume | Suitable amount |
| (5) Preservative | Suitable amount |
| (6) Water | Balance |

(Preparation)
(1)-(3), (5) and (6) were mixed and heated at 70° C. After cooling, (4) was added to the mixture to give a product. The thus obtained hair cream product exhibited an excellent styling property and excellent feeling on use.

EXAMPLE 3

Hair Tonic (Composition)

| (1) Ethanol | 50.0(%) |
|---|---|
| (2) Hinokitiol | 0.05 |
| (3) Menthol | 0.1 |
| (4) α-mono(isostearyl)glyceryl ether | 1.5 |
| (5) Perfume | suitable amount |
| (6) Colorant | suitable amount |
| (7) Water | balance |

(Preparation)
(1)-(7) were mixed at room temperature to give a product. The thus obtained hair tonic product exhibited an excellent feeling on use and imparted smoothness to hair.

EXAMPLE 4

Hair liquid (Composition)

| (1) Ethanol | 45.0(%) |
|---|---|
| (2) α-mono(isostearyl)glyceryl ether | 12.0 |
| (3) Propylene glycol | 2.0 |
| (4) Perfume | suitable amount |
| (5) Colorant | suitable amount |
| (6) Water | balance |

(Preparation)
(1)-(6) were mixed to give a product. The thus obtained hair liquid product exhibited an excellent styling property and excellent feeling one use.

EXAMPLE 5

Hair Cream (Composition)

| (1) α-mono(isopalmityl)glyceryl ether | 14.0(%) |
|---|---|
| (2) Polyoxyethylene stearyl ether | 1.5 |
| (3) Bees wax | 1.0 |
| (4) Perfume | suitable amount |
| (5) Preservative | suitable amount |
| (6) Water | balance |

(Preparation)
(1)-(3), (5) and (6) were mixed and heated at 70° C. After cooling, (4) was added to the mixture to give a product. The hair cream product exhibited an excellent styling property and excellent feeling in use.

EXAMPLE 6

Hair Tonic (Composition)

| | |
|---|---|
| (1) Ethanol | 50.0(%) |
| (2) Hinokitiol | 0.05 |
| (3) Menthol | 0.1 |
| (4) α-mono(isopalmityl)glyceryl ether | 11.0 |
| (5) Perfume | suitable amount |
| (6) Colorant | suitable amount |
| (7) Water | balance |

(Preparation)

(1)–(7) were mixed at room temperature to give a product. The hair tonic product exhibited excellent feeling in use and imparted smoothness to hair.

1. A method of imparting moisture, gloss and lubricity to hair without skin irritation comprising applying to the hair a preparation comprising 0.5–30 wt % of α-mono- (methyl-branched alkyl) glyceryl ether represented by the general formula (I):

$$R\text{-}OCH_2CH(OH)CH_2OH \qquad (I)$$

in which R represents a group of the following formula:

$$CH_3\text{—}(CH_2)_m\text{—}CH\text{—}(CH_2)_n\text{—}$$
$$|$$
$$CH_3$$

in which m is an integer of 2–14, n is an integer of 3–11 and m+n is an integer of 9–21, and the balance a carrier selected from the group consisting of hair tonic, hair conditioner, hair pomade, hair oil, hair cream, hair spray and hair setting lotion.

2. A method of treating hair according to claim 1, wherein the group of the formula is composed of over 75% of a group having 18 carbon atoms and m is an integer of 6–8.

* * * * *